United States Patent [19]

Takehira et al.

[11] Patent Number: 5,223,646
[45] Date of Patent: Jun. 29, 1993

[54] PROCESS FOR PRODUCING OPTICALLY ACTIVE ATENOLOL AND INTERMEDIATE THEREOF

[75] Inventors: Yoshikazu Takehira, Itami; Nobuaki Saragai, Amagasaki; Kazuhiro Kitaori, Itami, all of Japan

[73] Assignee: Daiso Company, Ltd., Osaka, Japan

[21] Appl. No.: 871,743

[22] Filed: Apr. 21, 1992

Related U.S. Application Data

[62] Division of Ser. No. 624,302, Dec. 7, 1990, Pat. No. 5,130,482.

[30] Foreign Application Priority Data

Dec. 27, 1989 [JP] Japan .................................. 1-344447

[51] Int. Cl.$^5$ .......................................... C07C 209/88
[52] U.S. Cl. .................... 564/165; 564/302; 564/304
[58] Field of Search ........................................ 564/165

[56] References Cited

U.S. PATENT DOCUMENTS

| | | | |
|---|---|---|---|
| 3,663,607 | 5/1972 | Barrett et al. | 260/501.1 |
| 3,836,671 | 9/1974 | Barrett et al. | 424/324 |
| 3,934,032 | 1/1976 | Barrett et al. | 424/324 |
| 4,876,371 | 10/1989 | Ito et al. | 549/517 |

FOREIGN PATENT DOCUMENTS

| | | | |
|---|---|---|---|
| 193227 | 9/1986 | European Pat. Off. | |
| 3147150 | 6/1983 | Fed. Rep. of Germany | 549/517 |
| 3500761 | 9/1986 | Fed. Rep. of Germany | |
| 40-21330 | 9/1965 | Japan | 549/517 |
| 50-77331 | 6/1975 | Japan | |
| 57-14586 | 1/1982 | Japan | 549/517 |
| 63-270651 | 11/1988 | Japan | |
| 1458393 | 12/1976 | United Kingdom | |
| 9007506 | 12/1990 | World Int. Prop. O. | 549/517 |

OTHER PUBLICATIONS

"Chem. Abstracts", vol. 111 (Nov. 1989), p. 753, Abstract #194562p.
Y. Tsuda et al., Chem. Phar. Bull., 29 (12), 1981, pp. 3593-3600.
M. J. Wilson et al., Journal of Chromatography 431 (1988), pp. 222-227.

*Primary Examiner*—Richard L. Raymond
*Attorney, Agent, or Firm*—Wegner, Cantor, Mueller & Player

[57] ABSTRACT

Improved process for producing an optically active atenolol useful as a β-adrenergic blocker for the treatment of angina pectoris, arrhythmia and hypertension, which comprising reacting a phenol compound with an optically active epihalohydrin to give an intermediate, optically active glycidyl ether compound, followed by reacting the intermediate with isopropylamine, and purification method of the optically active atenolol in high yield by means of forming a salt of atenolol with a Brønsted's acid whereby the salt of optically active atenolol having high optical purity can be separated from the salt of racemic atenolol by solid-liquid separation method.

4 Claims, No Drawings

PROCESS FOR PRODUCING OPTICALLY ACTIVE ATENOLOL AND INTERMEDIATE THEREOF

This application is a divisional of Ser. No. 07/624,302 filed Dec. 7, 1990, now U.S. Pat. No. 5,130,482.

TECHNICAL FIELD

This invention relates to an improved process for producing optically active atenolol and an intermediate thereof. More particularly, it relates to a process for producing an intermediate, optically active glycidyl ether compound and producing optically active atenolol from the intermediate, optically active glycidyl ether, and also to a method for isolation and purification of the optically active atenolol in a high yield.

PRIOR ART

It is known that atenolol (chemical name: 4-[2-hydroxy-3-[(1-methylethyl)amino]propoxy]benzeneacetamide) is useful as $\beta$-adrenergic blocker for the treatment of angina pectoris, arrhythmia and hypertension. It is also known that atenolol has 1-aryloxy-3-aminopropan-2-ol nucleus wherein the hydroxy-bonded carbon is an asymmetric carbon and hence includes optical isomers, R- and S-isomers, and the S-isomer thereof is particularly useful as $\beta$-adrenergic blocker in view of the superior pharmacological activities. It is reported that only S-isomer of atenolol has hypotensive activity and activity on brachycardia (cf. A.A. Pearson, T.E. Gaffney, T. Walle, P.J. Privitera; J. Pharmacol. Exp. Ther., 250 (3), 759, 1989).

It has been proposed to produce the optically active atenolol by the steps shown in the following scheme (cf. JP-A-50-77331, DE-A-2453324):

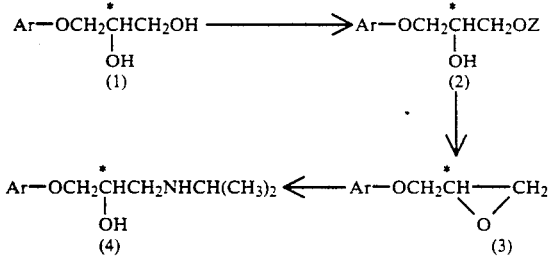

wherein Ar is

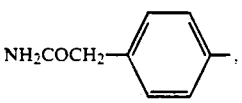

Z is a halogen atom or sulfonyloxy group, and * means asymmetric carbon.

However, this process has some disadvantages. That is, it requires multiple steps for obtaining the compound (1) from the starting D-mannitol; in the step of converting the primary hydroxy group of the compound (1) into the corresponding halogen or sulfonyloxy group, the carbamoylmethyl group ($NH_2COCH_2-$) on the aryl group is also reacted with the reactant and is converted into cyanomethyl group; due to production of a large amount of the by-product, the yield of the desired compound (4) is very low, less than 50%; and further, the secondary hydroxy group is also reacted with the reactant in some degree, and thereby, the intermediate glycidyl ether (3) has less purity such as 80% ee or lower. Accordingly, the above process is not suitable for the industrial process for producing the desired optically active atenolol.

It is also known that atenolol and analogues are prepared by reacting a phenol compound with epihalohydrin (e.g. epichlorohydrin) to obtain a glycidyl ether and then reacting the glycidyl ether with an amine compound (cf. U.S. Pat. Nos. 3,663,607, 3,836,671 and 3,934,032) as shown by the following scheme:

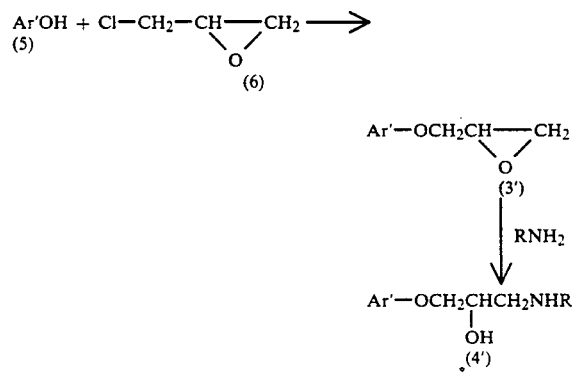

wherein Ar' is a substituted phenyl including

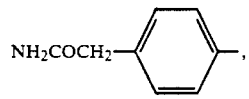

and R is a lower alkyl.

That is, the phenol compound (5) is reacted with an excess amount of epichlorohydrin (6) in the presence of catalytic amount of piperidine or a salt thereof at a temperature of 95 to 100° C. for several hours to give the glycidyl ether intermediate (3'), and the glycidyl ether is reacted with an alkylamine to give the desired 1-phenoxy-3-amino-2-propanol derivatives (4'). However, according this process even if an optically active epichlorohydrin (6) is used, racemization occurs in the reaction with the phenol compound (1) and hence an optical purity of the intermediate glycidyl ether (3') becomes less than 70% ee, and thereby an optical purity of the final product is also less than 70% ee. Moreover, this process requires a large amount of the expensive optically active epichlorohydrin, and even when the excess amount of epichlorohydrin is recovered, it can not be used because of its lower optical purity. Accordingly, this process is not suitable for producing an optically active atenolol and intermediate thereof, either.

It is also proposed to produce the 1-phenoxy-3-amino-2-propanol derivatives via an oxazolidinone intermediate [cf. Y. Tsuda, K. Yoshimoto, T. Nishikawa, Chem. Pharm. Bull., 29(12), 3593 (1981)]. However, when this process is applied to the production of atenolol, the $NH_2COCH_2-$ group is preferentially hydrolyzed under the conditions for ring-opening reaction of the oxazolidinone intermediate by alkali hydrolysis, and hence the desired atenolol can not be obtained.

Besides, it has also been studied to produce the desired optically active atenolol by optical resolution, but any practically useful method has never been found. It is reported that diastereomer of atenolol having a high purity is obtained from the racemic mixture by using (R,R)-O,O-di-p-toluoyltartaric acid anhydride (cf. Wilson M.J. et al., J. Chromatogr. (NLD) 431 (1), 222–227, 1988). However, this method requires a large amount of solvent and further it is technically very troublesome to recycle (R,R)-O,O-di-p-toluoyl-tartaric acid anhydride, and hence, this method is not suitable for the practical production of optically active atenolol.

BRIEF DESCRIPTION OF THE INVENTION

The present inventors have intensively studied as to improved process for producing optically active atenolol on industrial scale and have found that when the phenol compound is reacted with an optically active epihalohydrin (e.g. epichlorohydrin) in the presence of an alkali metal hydroxide at a lower temperature, the optically active intermediate glycidyl ether can be obtained in a high yield without occurrence of undesirable recemization, and thereby the desired optically active atenolol can be obtained by reacting the optically active intermediate glycidyl ether with isopropylamine in a usual manner in a high yield and high optical purity.

An object of the invention is to provide an improved process for producing optically active atenolol via optically active glycidyl ether intermediate. Another object of the invention is to provide a process for producing an optically active glycidyl ether which is useful for producing the optically active atenolol. A further object of the invention is to provide a method for isolation and purification of optically active atenolol.

DETAILED DESCRIPTION OF THE INVENTION

The process for producing optically active atenolol of this invention comprises reacting a compound of the formula:

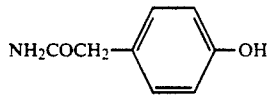

(I)

with an optically active epihalohydrin (e.g. epichlorohydrin) in the presence of 1 to 1.5 equivalent of an alkali metal hydroxide to the compound (I) in an aqueous solvent at a temperature of 0° to 35° C. to give an optically active glycidyl ether of the formula:

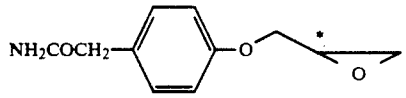

(II)

wherein * means asymmetric carbon, followed by reacting the optically active intermediate glycidyl ether (II) with isopropylamine in a conventional manner to give the desired optically active atenolol of the formula:

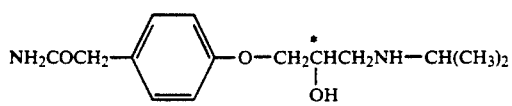

(III)

The aqueous solvent used in the above process includes water or a mixture of water with an organic solvent, such as alcohols (e.g. methanol, ethanol, isopropyl alcohol, etc.), ethers (e.g. diethyl ether, tetrahydrofuran, dioxane, etc.), hydrocarbons (e.g. hexane, heptane, benzene, toluene, etc.), halogenated hydrocarbons (e.g. dichloromethane, dichloroethane, etc.), ketones (e.g. acetone, methyl ethyl ketone, etc.), aprotic polar solvents (e.g. dimethylformamide, dimethyl sulfoxide, etc.), which may be used alone or combination of two or more thereof. The mixture of water and the organic solvent(s) may be homogeneous or heterogeneous mixture. When the reaction is carried out in an aqueous solvent, the optically active glycidyl ether (II) is precipitated as crystal in the reaction system and is easily separated by a conventional separation method. When water alone is used as the solvent and the starting materials and alkali metal hydroxide are used in a high concentration, the reaction mixture occasionally becomes viscous slurry, and hence, in such a case, it is preferable to use a mixture of water with an organic solvent. Water is usually used in an amount of 1 to 20 times larger amount by weight to the phenol compound (I). When a mixture of water and an organic solvent is used, the organic solvent is used in a ratio of 1 to 0.0001 part by volume to 1 part by volume of water. In order to make easier the precipitation of the product, there may be added an appropriate amount of an alkali metal chloride (e.g. sodium chloride, potassium chloride, etc.), an alkali metal carbonate (e.g. sodium carbonate, potassium carbonate, etc.), a sulfate (e.g. magnesium sulfate, sodium sulfate, etc.) to the reaction mixture.

The alkali metal hydroxide is preferably lithium hydroxide, sodium hydroxide or potassium hydroxide and is used in an amount of 1 to 1.5 mole to 1 mole of the phenol compound (I). When the alkali metal hydroxide is used in a too excess amount, it reacts disadvantageously with the starting epihalohydrin. The alkali metal hydroxide is usually used in the form of an aqueous solution having a concentration of 1 to 20% by weight.

The reaction can be carried out by adding the epihalohydrin to an aqueous alkali solution of the phenol compound (I), or alternatively by adding an alkali metal salt of the phenol compound of the formula:

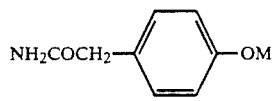

(wherein M is an alkali metal) in the form of a solid or an aqueous solution thereof to epihalohydrin. The epihalohydrin used in the reaction includes conventional epichlorohydrin, epibromohydrin, etc., but is preferably epichlorohydrin having high optical purity prepared by the process as disclosed in JP-A-61-132196. The epihalohydrin is preferably used in an amount of 1 to 3 moles, more preferably 1 to 2 moles, to 1 mole of the phenol compound (I).

The reaction may be carried out in the presence of a quaternary ammonium salt of the formula:

$R_1R_2R_3R_4N^+X^-$ (IV)

wherein $R_1$, $R_2$, $R_3$, and $R_4$ are the same or different and are each an alkyl having 1 to 16 carbon atoms (e.g. methyl, ethyl, propyl, butyl, pentyl, hexyl, heptyl, octyl, nonyl, stearyl, etc.), allyl, an aryl having 6 to 7 carbon atoms (e.g. phenyl, m-trifluoromethylphenyl, etc.), or benzyl, X is chlorine, bromine, iodine, $HSO_4^-$ or hydroxy. Specific examples of the quaternary ammonium salt are benzyltrimethylammonium bromide, benzyltriethylammonium chloride, β-methylcholine iodide, n-octyltrimethylammonium bromide, diallyldimethylammonium chloride, phenyltrimethylammonium hydroxide, tetra-n-butylammonium iodide, stearyltrimethylammonium bromide, cetyldimethylethylammonium bromide, tetra-n-butylammonium hydrosulfate. The quaternary ammonium compound is usually added in an amount of 0.001 to 5.0% by weight based on the weight of the phenol compound (I).

The reaction temperature is in the range of 0° to 35° C., preferably 5° to 30° C., more preferably 5° to 25° C. When the temperature is below 0° C., the reaction little proceeds and the aqueous reaction medium occasionally freezes, and on the other hand, when the temperature is over 35° C., the glycidyl ether (II) has less optical purity and the amount of the side reaction product is disadvantageously increased. Moreover, when the reaction temperature is higher, it tends to increase the degree of racemization and further the produced glycidyl ether (II) reacts with the starting phenol compound alkali metal salt to produce side reaction product. Accordingly, at the initial stage of the reaction, the reaction system is cooled to 0° to 20° C., and the temperature is gradually raised. When the reaction temperature is lower, the produced glycidyl ether (II) has higher optical purity. For example, when the reaction is carried out at 5° C., the produced glycidyl ether (II) has an optical purity of 96% ee. The reaction is usually carried out for 5 to 10 hours at room temperature, and for 10 to 48 hours at 5° C. When the reaction is carried out for too long period of time, it causes increase of the side reaction product which is hardly removable by filtration.

In the reaction, there is occasionally produced another side reaction product, halohydrin of the formula:

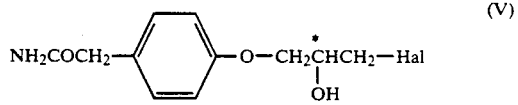

(V)

wherein Hal is a halogen atom (e.g. chlorine atom) and * means asymmetic carbon. However, this halohydrin can also be converted into the desired optically active atenolol by reacting it with isopropylamine, and hence, the contamination thereof does not affect on the process for producing optically active atenolol of the present invention.

With proceeding of the reaction, the optically active glycidyl ether (II) is precipitated, and the precipitated crystals can be isolated from the reaction mixture by a conventional method such as filtration, or the product may be isolated by extraction with an organic solvent (e.g. ethyl acetate). Alternatively, the glycidyl ether (II) may be used without isolating from the reaction mixture for the subsequent reaction with isoporpylamine, but in this case, it is necessary to neutralize the unreacted alkali metal hydroxide with an appropriate acid (e.g. hydrochloric acid) in order to prevent undesirable hydrolysis of the $NH_2COCH_2-$ group.

The optically active glycidyl ether (II) obtained by the above process has an optical purity of 90 to 96% ee. This product may be used in the subsequent reaction with isopropylamine, but alternatively may previously be purified by the following manner.

The optically active glycidyl ether (II) is recrystallized from an appropriate solvent, such as an alcohol having 1 to 6 carbon atoms (e.g. methanol, ethanol, isopropyl alcohol, n-butanol, t-butanol, hexanol, cyclohexanol, etc.), ketones having 3 t 6 carbon atoms (e.g. acetone, methyl ethyl ketone, methyl isopropyl ketone, methyl isobutyl ketone, cyclohexanone, etc.), organic acid esters (e.g. methyl acetate, ethyl acetate, ethyl butyrate, ethylene glycol diacetate, etc.), alkylnitriles having 1 to 4 carbon atoms (e.g. acetonitrile, propionitrile, butyronitrile, isobutyronitrile, etc.), which may be used alone or in combination of two or more thereof, preferably a combination of an alcohol and a ketone. By the recrystallization, the glycidyl ether can be obtained in an optical purity of 98% or higher.

The intermediate optically active glycidyl ether (II) thus obtained can easily be converted into the desired optically active atenolol (III) by reacting it with isopropylamine in a known method.

That is, the optically active glycidyl ether (II) (1 mole) is reacted with 3 to 50 moles of isopropylamine in a solvent such as water or a lower alcohol (e.g. methanol, ethanol, isopropyl alcohol, n-butanol), or in a mixture of water and an alcohol with stirring at 5° to 60° C. for 5 to 20 hours. The solvent is used in an amount of 3 to 100 parts by weight to 1 part by weight of the glycidyl ether (II) so that the glycidyl ether is uniformly dissolved in the solvent. When the glycidyl ether (II) contaminated with the side reaction product, halohydrin (V) is used, it is preferable to add an alkali metal carbonate (e.g. sodium carbonate, potassium carbonate) to the reaction system at the initiation or middle of the reaction in an amount of 1 to 5 moles to 1 mole of the halohydrin (V). When the reaction temperature is lower than 5° C., the reaction proceeds very slowly, but on the other hand, when it is higher than 60° C., the $NH_2COCH_2-$ group of the product is disadvantageously hydrolyzed under basic condition. Besides, in order to prevent the reaction of the produced atenolol with the glycidyl ether (II), it is preferable to carry out the reaction in such a manner that the glydiyl ether is added to isopropylamine in a solvent.

The reaction of the optically active glycidyl ether (II) and isopropylamine may also be carried out in the presence of a catalytic amount of a Lewis acid, such as iron chloride, aluminum chloride, trifluoroborone, magnesium halide, copper halide, nickel halide, cobalt halide, tin halide, etc. at room temperature (cf. JP-A-57-95946).

The optically active glycidyl ether (II) obtained by the present invention can also be used for reacting with other alkylamines to produce other optically active β-adrenergic blockers. Thus, an object of this invention is also to provide a process for producing the optically active glycidyl ether per se.

According to the process of the present invention as mentioned hereinabove, the optically active atenolol can be obtained in an optical purity of 98% or higher in a high yield, but it requires to repeatedly recrystallize the intermediate optically active glycidyl ether (II) for obtaining the highly pure optically active atenolol.

The present inventors have further intensively studied a method for isolation and purification of the optically active atenolol more easily without necessity of the repeated recrystallization of the intermediate glycidyl ether, and have found that the atenolol per se has a small difference in the solubility between the racemic mixture and the optically active product and hence it is difficult to isolate the optically active atenolol by utilizing the difference in solubility, but when the atenolol is formed a salt with Brønsted's acid, the salt shows a big difference in the solubility between the optically active product and the racemic mixture, and by utilizing this difference in the solubility, the desired optically active atenolol can easily be separated.

Thus, another object of the invention is to provide an improved method for isolating and separating optically active atenolol in high optical purity and yield.

The purification method of this invention comprises treating the atenolol (III) obtained in the above-mentioned process with a Brønsted's acid to form a salt thereof, separating selectively a salt of optically active atenolol having higher solubility from a salt of racemic atenolol having lower solubility in a solvent utilizing the difference of the solubility in the solvent, followed by removing the acid moiety from the thus separated salt.

The selective separation of the salt of optically active atenolol with Brønsted's acid can be carried out by extracting the salt having higher optical purity from the solid salt mixture having lower optical purity with a solvent, or dissolving the salt mixture having lower optical purity in a solvent, removing the precipitated salt which has high content of racemic mixture and isolating the desired salt having high optical purity from the liquid phase.

The Brønsted's acid used in this invention includes inorganic acids, organic mono- or di-carboxylic acids, organic sulfonic acids and phenols, which may be used alone or in combination of two or more thereof. Suitable examples of the acid are inorganic acids such as hydrogen chloride, hydrogen bromide, hydrogen iodide, sulfuric acid, phosphoric acid; organic carboxylic acids such as formic acid, acetic acid, propionic acid, butyric acid, 3-methylpentanoic acid, 2,2-dimethylpropionic acid, oxalic acid, succinic acid, glutaric acid, adipic acid, maleic acid, fumaric acid, citraconic acid, or aromatic acids such as benzoic acid, phthalic acid, terephthalic acid, cinnamic acid, furancarboxylic acid, pyridinecarboxylic acid, or phenylacetic acid wherein the aromatic ring may optionally be substituted by a member selected from a halogen atom (e.g. fluorine, chlorine, bromine, iodine), nitro, cyano, hydroxy, an alkyl having 1 to 9 carbon atoms, an alkenyl having 2 to 9 carbon atoms, an alkyloxy having 1 to 9 carbon atoms, or an acyl, or tartaric acid or its acyl derivatives (i.e. the hydroxy group is acylated with benzoyl, cyclohexanecarbonyl, or toluoyl), or glutamic acid; organic sulfonic acids such as methanesulfonic acid, trifluoromethanesulfonic acid, camphorsulfonic acid, or aromatic sulfonic acids such as benzenesulfonic acid, naphthalenesulfonic acid wherein the aromatic ring may optionally be substituted by a member selected from a halogen atom (e.g. fluorine, chlorine, bromine, iodine), nitro, cyano, hydroxy, an alkyl having 1 to 9 carbon atoms, an alkenyl having 2 to 9 carbon atoms, an alkyloxy having 1 to 9 carbon atoms, or an acyl; phenols such as phenol or naphthol wherein the aromatic ring may optionally be substituted by a member selected from a halogen atom (e.g. fluorine, chlorine, bromine, iodine), nitro, cyano, hydroxy, an alkyl having 1 to 9 carbon atoms, an alkenyl having 2 to 9 carbon atoms, an alkyloxy having 1 to 9 carbon atoms, or an acyl. Among these, the preferred ones are benzoic acid having optionally a substituent, benzenesulfonic acid having optionally a substituent, oxalic acid, adipic acid, fumaric acid, maleic acid, and cinnamic acid.

The Brønsted's acid is used in an amount of 0.5 to 2 equivalents to the atenolol.

The reaction for forming the salt of atenolol and Brønsted's acid can be carried out by a known method. For example, in case of using a solid or liquid acid, atenolol is directly mixed with the acid, or alternatively, both components are added to a solvent, wherein the salt is formed. In case of a gaseous acid such as hydrogen chloride, the gaseous acid is blown into an appropriate solvent (e.g. water, methanol, ethanol, chloroform, ethyl ether, etc.) and thereto atenolol is added, or alternatively, the gaseous acid is blown into a solution containing atenolol.

When the salt is formed in a solution, the solvent is distilled off and the solid material is separated and is added to a solvent of purification as mentioned hereinafter, but it is preferable to form directly the salt in said solvent for purification.

Thus, the atenolol having lower optical purity is firstly formed in a salt with Brønsted's acid, and the formed salt mixture is subjected to separation into a salt having high optical purity and a salt having low optical purity in the following manner.

The salt mixture formed above is dissolved in a solvent, whereby the salt having high optical purity is dissolved in the solvent and the salt having low optical purity is remained as a solid, and hence, by distilling the solution the desired salt having high optical purity can be isolated.

The isolation can be carried out, for example, by a crystallization method or an extraction method.

The crystallization method can be carried out by firstly dissolving the atenolol salt mixture in a solvent, solidifying the racemic salt having lower optical purity by a conventional precipitation method (e.g. cooling, concentration, or addition of a less-soluble solvent, or a combination thereof), and then subjecting to a conventional solid-liquid separation method (e.g. filtration, centrifugation, etc.) to give the desired atenolol salt having higher optical purity.

The solvent used for the above method includes any solvents other than amine solvents which affects on the forming of a salt. Suitable examples of the solvent are water, alcohols having 1 to 8 carbon atoms (e.g. methanol, ethanol, 2-propanol, etc.), halogenated hydrocarbons (e.g. chloroform, etc.), ketones (e.g. acetone, methyl ethyl ketone, etc.), esters (e.g. methyl acetate, ethyl acetate, etc.), nitriles (e.g. acetonitrile, propionitrile, etc.), nitroalkanes (e.g. nitromethane, nitroethane, etc.), hydrocarbons (e.g. hexane, n-heptane, cyclohexane, etc.), ethers (e.g. diethyl ether, tetrahydrofuran, dioxane, ethylene glycol diethyl ether, etc.), pyrrolidone, N-methylpyrrolidone, dimethylformamide, hexamethylphophoric triamide, dimethyl sulfoxide, and the like, which may be used alone or in combination of two or more thereof.

More specifically, the crystallization method is carried out as follows:

The atenolol having low optical purity (1 mole) and p-toluic acid (1 mole) are dissolved in acetone (5 to 50 liters) with heating and the mixture is stirred at 0° to 15° C. for 5 to 24 hours. The precipitated crystals are removed by filtration, and the mother liquor is concentrated to give an optically active atenolol p-toluate with having higher optical purity, for example a salt having an optical purity of 98% ee or more from a salt having an optical purity of 91% ee in a yield of 50 to 80%. In this method, when benzoic acid is used instead of p-toluic acid and chloroform is used instead of acetone, similar result is obtained. When p-t-butylbenzoic acid is used instead of p-toluic acid in the above method, the produced salt is hardly soluble in a solvent, and hence, it is necessary to use a solvent having higher solubility such as ethanol or 2-propanol instead of acetone.

The extraction method is carried out in the following manner.

The atenolol salt mixture (having low optical purity) is previously crushed in an appropriate particle size and is subjected to extraction with a solvent by continuous or batch system. In the continuous extraction, the solid salt mixture is packed in a plural of columns which are arranged in-line, to which the solvent is flowed. According to this method, since the contact between the solid product and the liquid phase is very short, it is preferable to allow to stand the mixture for a fixed period of time. It can also be carried out by a continuous countercurrent extraction method with Hildebrand extractor.

When the separation is carried out by batch system, the solid product and the solvent for extraction are charged in an extractor, and after dipping the solid product in the solvent for a fixed period of time, optionally with stirring, the extracting solvent is drained from the bottom of the vessel through a filter. According to this method, a plural of extractors are arranged in-line, wherein it is preferable to extract by a countercurrent extraction method, that is, it is extracted so that the fresh solid product is contacted with the final extracting solvent. The temperature for the extraction may vary depending on the solubility of the starting solid product in the solvent, but is usually in the range of from room temperature to the reflux temperature of the solvent.

The solvent includes the same solvents as used in the above crystallization method.

The salt of atenolol with benzoic acid or sulfonic acids can be purified merely by stirring it in a solvent (e.g. chloroform) and filtering off the undissolved solid materials, or it may be purified by the continuous extraction as mentioned above.

In order to increase the solubility of the atenolol salt, there may be added an additive such as amines and carboxylic acid salts to the extraction system.

The precipitated salts or undissolved solid materials removed from the mixture in the above-mentioned method contains still optically active atenolol, and hence, such impure salts may be subjected repeatedly to the above purification methods, by which the desired optically active atenolol having an optical purity of 98% ee or more can further be isolated.

The optically active atenolol salt having high optical purity isolated by the above methods is then subjected to the subsequent step of removing the acid moiety to isolate the desired optically active atenolol having high optical purity in the free form. The removal of the acid moiety may be carried out as to the mother liquor obtained in the above methods or alternatively as to the salt isolated from the solution.

The removal of the acid moiety from the isolated salt can be carried out by neutralizing the salt with a base in a solvent to separate it into an acid and a base, or by using an ion exchange resin.

The base used for the neutralization of the salt includes inorganic bases and inorganic salts such as hydroxides, carbonates or hydrogen carbonates of an alkali metal or alkaline earth metal (e.g. sodium, potassium lithium, barium, calcium, magnesium, etc.), or sodium hydride, or a mixture thereof; organic bases such as triethylamine, isopropylamine, pyridine, 4-N,N-dimethylaminopyridine, and the like, or a mixture thereof.

The above neutralization of the atenolol salt gives a salt of the acid moiety and base, and the resulting salt of the acid moiety and base is removed from the optically active atenolol. The removal may be carried out by various methods which may vary depending on the kinds of the acid moiety and base. For example, in some cases, there is formed a hardly soluble salt with an inorganic base, and in such cases, after removing the salt, for example, by filtering, the optically active atenolol is extracted from the filtrate with a solvent. In other cases, an easily soluble salt is formed, and in such cases, the soluble salt is dissolved in a solvent in which the optically active atenolol is little soluble, by which the optically active atenolol can be separated from the salt. The separation may also be carried out by a countercurrent extraction method.

The ion exchange resin includes cation exchange resins and anion exchange resins. Suitable examples of commercially available ion exchange resins are Amberlites ®, Amberlysts ®, Dowexes ®, and the like, but it is not limited thereto.

The method using an ion exchange resin can be carried out either batch system or with a column. Since atenolol is very soluble in water, it is preferable to isolate it with a solution of an ion exchange resin such as Amberlyst-15 ® in an organic solvent (e.g. alcohols), since the concentration of the solution and the precipitation of the desired atenolol are effectively carried out.

The solvent used in the above neutralization method and the method with an ion exchange resin may vary depending on the kinds of the bases and ion exchange resins, but includes water, alcohols (e.g. methanol, ethanol, 2-propanol, etc.), ketones (e.g. acetone, methyl ethyl ketone, etc.), esters (ethyl acetate, butyl acetate, etc.), nitriles (e.g. acetonitrile, propionitrile, etc.), nitro compounds (e.g. nitromethane, nitrobenzene, etc.), hydrocarbons (e.g. benzene, toluene, hexane, cyclohexane, etc.), halogenated hydrocarbons (e.g. chloroform, dichloromethane, chlorobenzene, etc.), ethers (e.g. diethyl ether, tetrahydrofuran, dioxane, ethylene glycol diethyl ether, etc.), amides (e.g. pyrrolidone, N-methylpyrrolidone, dimethylacetamide, etc.), hexamethylphsophoric triamide, dimethyl sulfoxide, and the like.

The method using an ion exchange resin can specifically be carried out in the following manner but is not limited thereto.

Amberlyst-15 ® which has an equivalent ion exchanging ability against optically active atenolol p-toluate is packed in a column (solvent: methanol), and a solution of optically active atenolol p-toluate in methanol is passed through the column from the top thereof, and then methanol is passed through until p-toluic acid is no more dissolved out. Thereafter, a methanol solution containing an amine compound (e.g. isopropylamine), an aqueous ammonia, etc. are passed to separate the optically active atenolol, and the solvent is distilled off from the resulting fraction to give the desired atenolol crystals. If necessary, the optically active atenolol may be recrystallized from an appropriate solvent such as alcohols, esters or ketones as mentioned above.

EXAMPLES

This invention is illustrated by the following Examples but should not be construed to be limited thereto.

Example 1

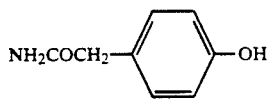

(3.02 g, 0.02M) is dissolved in a mixture of sodium hydroxide (0.96 g) and water (9.69 g), and the mixture is cooled to 3° C. and thereto added R—(—)—epichlorohydrin ($[\alpha]^{21}_D$ —35.0°, 1.85 g) with stirring, and the mixture is stirred from 3 hours while returning to room temperature. The precipitated crystals are separated by filtration, washed with water, and dried in vacuo in the presence of phosphorus pentoxide to give S—(+)-glycidyl ether (II) (2.66 g, 64%).

m.p. 161-162° C.

$[\alpha_D^{21}+9.6°$ (c=1.0, methanol). [data in literature, DE-2453324, m.p. 147-149° C., $[\alpha]_D^{21}+4.8°$ (c=1.0, methanol)].

NMR (DMSO-d$_6$) δ: 2.65-2.73 (1H, m, CH), 2.83 (1H, dt, J=1.1, 5.1 Hz, CH), 3.29 (2H, s, CH$_2$), 3.33 (1H, m, CH), 3.80 (1H, ddd, J=—11.4, 1.1, 6.6 Hz, CH), 4.29 (1H, ddd, J=—11.4, 1.1, 2.6 Hz, CH), 6.82 (1H, br s, NH), 6.89 (2H, J=7.7 Hz, ArH), 7.17 (2H, d, J=7.7 Hz, ArH), 7.39 (1H, br s, NH).

Example 2

In the same manner as described in Example 1 except that S-(+)-epichlorohydrin ($[\alpha]_D^{21}+35.0°$) is used instead of R-(—)-epichlorohydrin, there is obtained R-(—)-glycidyl ether (II) (2.88 g).

$[\alpha]_D^{21}-9.54°$ (c=1.0, methanol).

Example 3

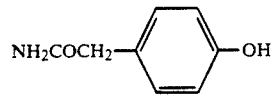

(20.09 g, 0.133M) is suspended in a mixture of potassium hydroxide (5.6 g), water (50 g) and methanol (5 g), and thereto is added dropwise S-(+)-epichlorohydrin ($[\alpha_D^{21}+34.2°$, 9.31 g) at 11° C. with stirring, and the mixture is stirred while raising the temperature up to 30° C. over a period of 3 hours. The resulting product is separated by filtration, washed with water and dried in vacuo in the presence of phosphorus pentoxide to give a mixture of R-(—)-glycidyl ether (II) and halohydrin (IV) (about 1:1, 17.9 g, yield, 33.5% and 26.8%, respectively).

Example 4

S-(+)-glycidyl ether (II) obtained in Example 1 (2.66 g) is added to a mixture of methanol (24.8 g) and isopropylamine (21.6 g), and the mixture is refluxed by heating with stirring for 6 hours. The reaction mixture is distilled under reduced pressure to remove the solvent, and the residue is purified by silica gel column chromatography (chloroform : methanol=20:1) to give S-(—)-atenolol (III) (3.04 g, 89%). This product has an optical purity of 93% ee when analyzed by HPLC with Chiralcel OD ®.

m.p. 151.0-152.5° C.

$[\alpha]_D^{21}$ —15.57° (c=1.0, 1N HCl).

[data in literature, DE-2453324, m.p. 151.3-153° C., $[\alpha]_D^{21}$ —13.6° (c=1.0, 1N HCl)].

Example 5

A mixture of R-(—)-glycidyl ether (II) and halohydrin (IV) (about 1 : 1, 8.77 g) obtained in Example 3 is added to a mixture of methanol (80 g) and isopropylamine (80 g), and the mixture is refluxed by heating with stirring for 5 hours. To the mixture is added sodium carbonate (3 g), and the mixture is further stirred with heating for 2 hours. The reaction mixture is distilled under reduced pressure to remove the solvent, and the residue is purified by silica gel column chromatography to give R-(+)-atenolol (III) (8.89 g, 85%). This product has an optical purity of 90% ee when analyzed by HPLC with Chiralcel OD ®.

m.p. 151.5-152.8° C.

$[\alpha]_D^{21}+15.0°$ (c=1.0, 1N HCl).

$^1$HNMR (DMSO-d$_6$) δ: 0.99 (6H, d, J=6.2 Hz, CH$_3$), 2.60-2.75 (2H, m, CH$_2$), 3.28 (2H, s, CH$_2$), 3.30-3.40 (1H, m, CH), 3.77-3.96 (3H, m, CH$_2$, CH), 6.80 (1H, br s, NH), 6.86 (2H, d, J=7.7 Hz, ArH), 7.17 (2H, d, J=7.7 Hz, ArH), 7.37 (1H, br s, NH).

EXAMPLE 6

S-(+)-glycidyl ether (II) obtained in Example 1 is recrystallized from methanol to give a purified product (II) [m.p. 167.3-168.6° C., $[\alpha]_D^{21}+10.8°$, (c=0.5, methanol)]. This product is reacted with isopropylamine in the same manner as described in Example 4 to give S-(—)-atenolol (III). This product has an optical purity of 98.3% ee when analyzed by HPLC with Chiralcel OD ®.

Example 7

R-(—)-glycidyl ether (II) obtained in Example 3 is recrystallized from acetone to give a purified product (II) [m.p. 166.2-167.9° C., $[\alpha]_D^{21}$ —10.6°, (c=0.5, methanol)]. This product is reacted with isopropylamine in the same manner as described in Example 4 to give R-(+)-atenolol (III). This product has an optical purity of 98.1% ee when analyzed by HPLC with Chiralcel OD ®.

Example 8

A mixture of R-(—)-epichlorohydrin (27.6 g) and water (21 g) is stirred under cooling at 5° C., and thereto is added dropwise a solution of

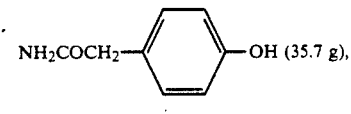

benzyltrimethylammonium chloride (0.18 g) and sodium hydroxide (9.44 g) in water (158.36 g) over a period of one hour, and the mixture is stirred at 5° C. for 51 hours. After confirming that the reaction proceeds 97% by HPLC analysis, the excess sodium hydroxide is neutralized with 3.5% hydrochloric acid at the same temperature. The reaction mixture is added to isopropylamine (264 g) under cooling at 10° C. with stirring over a period of one hour. After raising the temperature of the reaction mixture to 20° C., and the mixture is further stirred for 3.5 hours (the completion of the reaction is confirmed by HPLC). The reaction mixture is concentrated under reduced pressure until crystals are precipitated. After cooling, the product is separated by filtration with suction, dried in vacuo to give crude atenolol (III) (51.85 g, 72.2%). According to analysis by HPLC, this product has a chemical purity of 87.8% and an optical purity of 94.8% ee.

Example 9

S-atenolol (optical purity, 91% ee, 4.43 g) and p-toluic acid (2.28 g) are dissolved in acetone (300 ml) by heating, and the mixture is allowed to stand overnight at room temperature. The precipitated crystals are separated by filtration, and the filtrate is concentrated under reduced pressure to give S-atenolol toluate having an optical purity of 98.8% ee (5.01 g).

The precipitated crystals separated above (1.7 g) is S-atenolol toluate having an optical purity of 76.5% ee.

The S-atenolol toluate having an optical purity of 98.8% ee (5.01 g) obtained above is treated with ion exchange resin (Amberlyst 15 ®, manufactured by Rohm & Haas), and after removing the free toluic acid with methanol, the desired product is eluted with a mixture of isopropylamine and methanol to give S-atenolol having an optical purity of 98.3% ee (2.91 g).

$[\alpha]_D^{21} -16.7°$ (c=1.0, 1N HCl).
m.p. 150.9-152.2° C.
[data in literature, DE-2453324, $[\alpha]_D^{21} -13.6°$ (c=1.0, 1N HCl)].

The optical purity of the atenolol and a salt thereof is measured by HPLC analysis with "Chiralcel OD ®" (hereinafter the same).

Example 10

S-atenolol toluate having an optical purity of 71.1% ee (3.44 g) is recrystallized from 99.5% ethanol (25 ml) at room temperature. The precipitated salt (1.49 g) and the salt further obtained from the mother liquor (1.71 g) have an optical purity of 59.7% ee and 80.2% ee, respectively.

Example 11

R-atenolol benzoate having an optical purity of 94.3% ee (0.96 g) is stirred in chloroform (22 ml) at room temperature for 4 hours. The undissolved product (0.20 g) and the crystals obtained from the mother liquor (0.76 g) have an optical purity of 76.7% ee and 99.4% ee, respectively, when analyzed by HPLC.

The salt having an optical purity of 99.4% ee is treated with "Amberlyst-15 ®" in the same manner as described in Example 9 to give R-atenolol having an optical purity of 99.4% ee.
$[\alpha]_D^{21} +16.7°$ (c=1.0, 1N HCl).

Example 12

R-atenolol having an optical purity of 96% ee (0.66 g) and p-t-butylbenzoic acid (0.45 g) are added to 95 % ethanol (25 ml) at room temperature, and the precipitated crystals (1.49 g) and the crystals further obtained from the mother liquor (1.71 g) have an optical purity of 78.9% ee and 99.3% ee, respectively. The R-atenolol p-t-butylbenzoate having an optical purity of 99.3% ee has a melting point of 140-142° C.

Example 13

S-atenolol having an optical purity of 91.2% ee (0.66 g) and p-chlorobenzoic acid (0.40 g) are stirred in chloroform (20 ml) at room temperature for 5 hours, and the precipitated crystals (0.28 g) and the crystals further obtained from the mother liquor (0.74 g) have an optical purity of 70.3% ee and 98.5% ee, respectively.

Example 14

R-atenolol having an optical purity of 92.4% ee (0.66 g) and p-toluenesulfonic acid (0.50 g) are stirred in chloroform (60 ml) at room temperature for 5 hours, and the precipitated crystals (0.76 g) and the crystals further obtained from the mother liquor (0.40 g) have an optical purity of 86.6% ee and 94.1% ee, respectively.

Example 15

R-atenolol having an optical purity of 93.9% ee (0.66 g) and p-nitrophenol (0.348 g) are dissolved in 95% ethanol and thereto is added ethyl acetate (200 ml) at room temperature, and the precipitated crystals are separated by filtration. The precipitated crystals (0.38 g) and the crystals further obtained from the mother liquor (0.72 g) have an optical purity of 90.0% ee and 95.4% ee, respectively.

Example 16

S-atenolol hydrochloride having an optical purity of 90.9% ee (522 mg) is recrystallized from 2-propanol (20 ml) at room temperature. The precipitated crystalline salt (0.28 g) and the crystals further obtained from the mother liquor (0.24 g) have an optical purity of 87.8% ee and 95.2% ee, respectively.

Example 17

R-atenolol having an optical purity of 95.1% ee (0.652 g) and succinic acid (289 mg) are dissolved in 2-propanol (20 ml) by heating at 80° C. and allowed to cool to room temperature. The precipitated crystals are separated by filtration, and the filtrate is concentrated under reduced pressure to give R-atenolol succinate having an optical purity of 100% ee (430 mg).

The crystals precipitated above are R-atenolol succinate having an optical purity of 91.5% ee.

Example 18

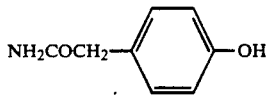

(15.33 g) and lithium hydroxide monohydrate (4.27 g) are dissolved in water (40 g) at 30° C., and the mixture is cooled to 5° C. and thereto added R-epichlorohydrin (optical purity: 98% ee, 9.25 g) with stirring, and the mixture is stirred from 24 hours at the same temperature. The precipitated crystals are separated by filtration, washed with water, and dried in vacuo in the presence of phosphorus pentoxide to give S-glycidyl ether (II) (10.56 g).

The S-glycidyl ether (II) (10.56 g) is added to a mixture of isopropylamine (65 g) and methanol (65 g) and the mixture is refluxed by heating with stirring for 15 hours. The reaction mixture is distilled under reduced pressure to remove the solvent and thereto is added acetone to crystalize the product to give S-atenolol having an optical purity of 96.5% ee (10.77 g).

The S-atenolol having an optical purity of 96.5% ee (10.77 g) thus obtained and p-toluic acid (5.54 g) are dissolved in acetone (1 liter) by heating with stirring and the mixture is stirred at room temperature for 10 hours. The precipitated crystals are separated by filtration and the filtrate is concentrated under reduced pressure to give S-atenolol p-toluate having an optical purity of 98.5% ee (14.47 g).

The crystals precipitated above (1.41 g) are S-atenolol p-toluate having an optical purity of 80.5% ee.

Example 19

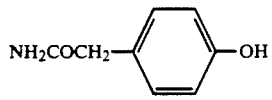

(7.67 g) and sodium hydroxide (2.13 g) are dissolved in water (40 g), and the mixture is cooled to 5° C. and thereto is added S-epichlorohydrin (optical purity: 98% ee, 4.7 g) with stirring, and the mixture is stirred for 16 hours at the same temperature to give R-glycidyl ether (II) (5.50 g).

The R-glycidyl ether (II) (5.50 g) thus obtained is added to a mixture of isopropylamine (39.2 g) and methanol (40 g) and the mixture is refluxed by heating with stirring for 10 hours. The reaction mixture is distilled under reduced pressure to remove the solvent and thereto is added acetone to crystalize the product to give R-atenolol having an optical purity of 95.8% ee (5.60 g).

The R-atenolol having an optical purity of 95.8% ee (5.60 g) thus obtained and benzoic acid (2.63 g) are dissolved in chloroform (90 ml) by heating and the mixture is stirred for 8 hours. The crystals precipitated at room temperature are separated by filtration and the filtrate is concentrated under reduced pressure to give R-atenolol benzoate having an optical purity of 99.4% ee (6.86 g).

The crystals precipitated above (1.31 g) are R-atenolol benzoate having an optical purity of 77.0% ee.

Example 20

In the same manner as described in Example 19 except that the reaction of

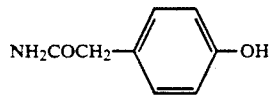

and sodium hydroxide is carried out at 20° C., there is obtained R-glycidyl ether (II) (6.5 g). The R-glycidyl ether (II) (6.5 g) is reacted with isopropylamine to give R-atenolol having an optical purity of 91.2% ee (6.3 g).

The R-atenolol having an optical purity of 91.2% ee (6.3 g) thus obtained is dissolved in chloroform (300 ml) by heating, and thereto is blown hydrogen chloride gas until it is saturated. The mixture is concentrated under reduced pressure, and the resulting hydrochloride (7.16 g) is dissolved in 2-propanol (400 ml) by heating, and then the mixture is stirred at room temperature for 8 hours. The precipitated crystals are separated by filtration and the filtrate is concentrated under reduced pressure to give R-atenolol hydrochloride having an optical purity of 96.2% ee (3.50 g).

The crystals precipitated above (3.66 g) are R-atenolol having an optical purity of 86.5% ee.

Reference Example 1

S-atenolol having an optical purity of 92% ee (0.65 g) is dissolved in acetone (28 ml) by heating, and the mixture is concentrated to 10 ml. After allowing to cool, the precipitated crystals are separated by filtration to give crystals have an optical purity of 92% ee (0.32 g).

Reference Example 2

R-atenolol having an optical purity of 88% ee (3.5 g) is dissolved in 2-propanol (30 ml) by heating, and the mixture is allowed to cool. The precipitated crystals are separated by filtration to give R-atenolol having an optical purity of 89% ee (2.8 g).

What is claimed is:

1. A process for producing an optically active atenolol having a high optical purity, which comprises reacting an atenolol having lower optical purity with a Brønsted's acid to form a salt thereof, separating selectively a salt of optically active atenolol having higher solubility from a salt of racemic atenolol having lower solubility in a solvent utilizing the difference of the solubility in the solvent, followed by removing the acid moiety from the thus-separated salt of optically active atenolol having high solubility.

2. The process according to claim 1, wherein the atenolol salt having higher optical purity is obtained by extracting from the solid atenolol salt having lower optical purity.

3. The process according to claim 1, wherein the separation of the atenolol salt having higher optical purity is carried out by dissolving the atenolol salt having lower optical purity in a solvent, precipitating solid materials having a high content of racemic atenolol salt, and then isolating the atenolol salt having higher optical purity by solid-liquid separation method.

4. The process according to claim 1, wherein the Brønsted's acid is a member selected from a hydrogen halide, sulfuric acid, phosphoric acid, organic mono- or di-carboxylic acids, organic sulfonic acids, and phenols.

* * * * *